Figure 1:
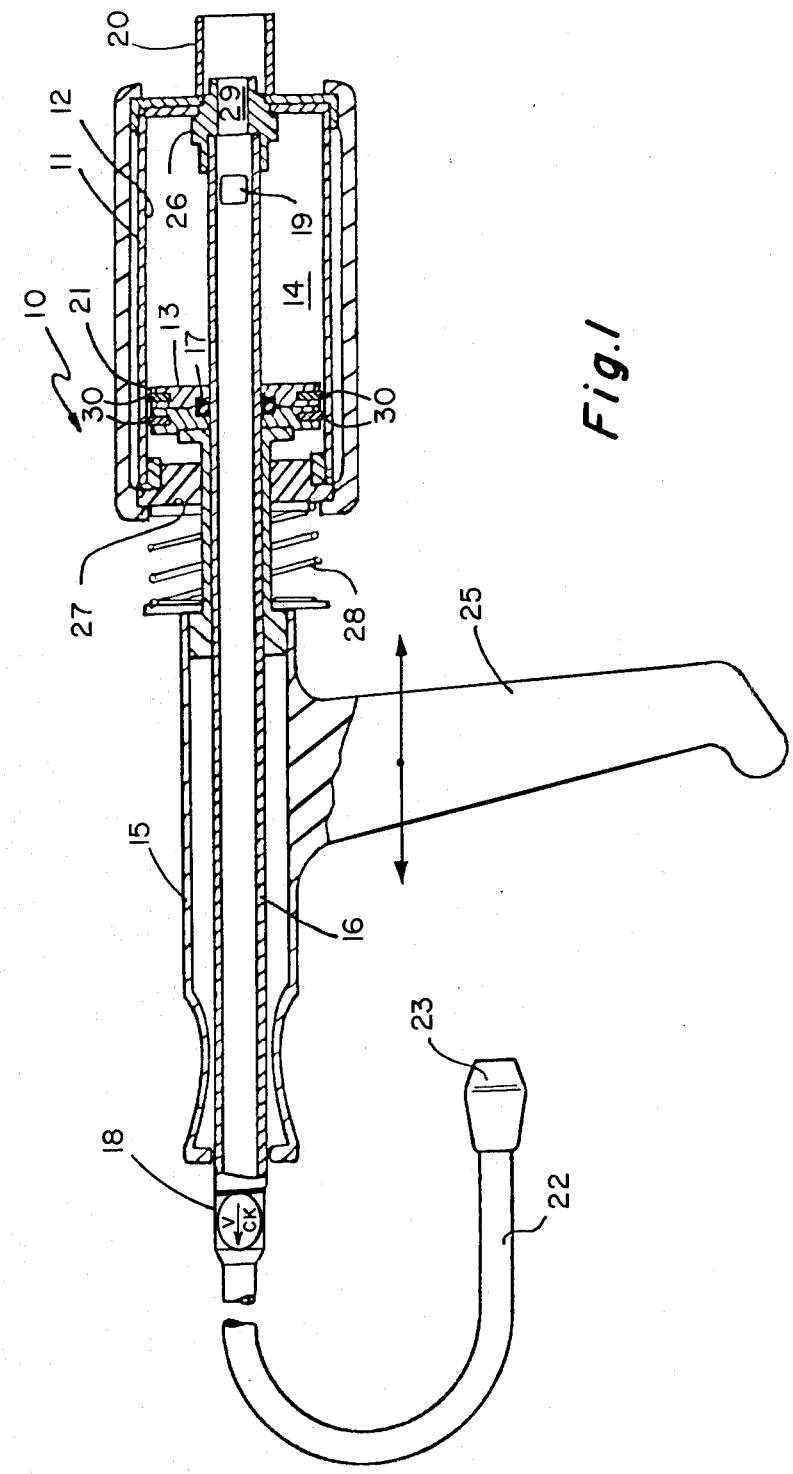
Figure 2:
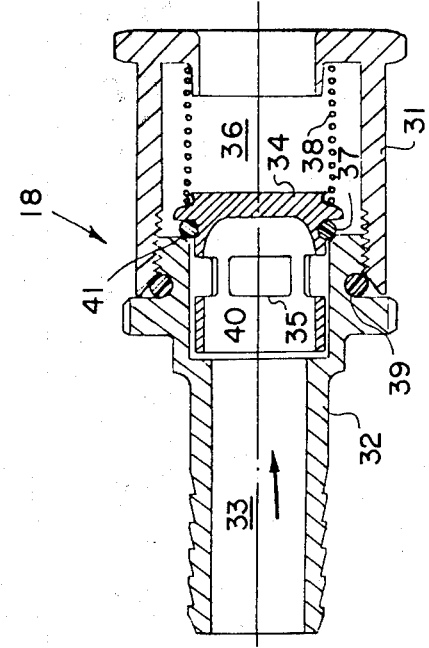

United States Patent [19]

Reynolds

[11] 4,359,050

[45] Nov. 16, 1982

[54] DRENCH GUN

[75] Inventor: Mervyn F. Reynolds, New South Wales, Australia

[73] Assignee: N. J. Phillips Pty. Ltd., New South Wales, Australia

[21] Appl. No.: 105,177

[22] Filed: Dec. 19, 1979

[30] Foreign Application Priority Data

Jan. 19, 1979 [AU] Australia .............................. PD7407

[51] Int. Cl.[3] .............................................. A61D 7/00
[52] U.S. Cl. .................................... 128/223; 128/234; 128/239
[58] Field of Search ........... 128/223, 222, 239, 213 R, 128/234, 235, 237, 218 P, 230, 200.14, 200.22, 200.23, 218 R, 220, 221, 224, 238; 222/378

[56] References Cited

U.S. PATENT DOCUMENTS

| 1,830,295 | 11/1931 | Scott ................................. 222/378 X |
| 4,020,838 | 5/1977 | Phillips et al. ....................... 128/234 |
| 4,204,539 | 5/1980 | Brugge .............................. 128/223 |

FOREIGN PATENT DOCUMENTS

| 532457 | 2/1922 | France ................................. 128/234 |
| 2312225 | 12/1976 | France ............................... 128/223 |

Primary Examiner—Henry J. Recla
Attorney, Agent, or Firm—Ladas & Parry

[57] ABSTRACT

A drench gun having a nozzle, an interacting sleeve and piston to eject drench through the nozzle, and wherein the nozzle is generally "U" shaped and the gun adapted to be used by one hand of an operator.

4 Claims, 1 Drawing Figure

DRENCH GUN

The present invention relates to liquid dispensing guns and more particularly but not exclusively to drench guns for the dosing of animals.

It is desirable in devices of this kind that the liquid inlet and outlet of the gun remains stationary upon operation of the trigger of the gun. Despite this feature being desirable, many guns produced have a liquid inlet or outlet which moves in co-ordination with the trigger, which movement makes it difficult to hold the gun during use thereof. Additionally, it is a disadvantage of some guns that both hands of the operator are required in order to manipulate the gun during use.

It is an object of the present invention to overcome or substantially ameliorate the above disadvantages.

There is disclosed herein a drench gun to deliver a dosage of drench into the mouth of a beast, said gun including a generally "U" shaped nozzle having a free end portion to be engaged within the mouth of the beast, a conduit attached to the other end portion of said nozzle and extending therefrom in the general direction of extension of the free end of the nozzle engaged within the beast's mouth, a hollow cylinder mounted on said conduit so as to be co-axial and co-extensive therewith, said cylinder being closed at one end and open at the other end which is located nearer said nozzle than said closed end, a piston slidably mounted on the conduit and slidably engaged within the cylinder so as to define within the cylinder a variable volume working space, a sleeve fixed to the piston and extending from within said cylinder enabling it to be gripped by a user of the gun to vary the volume of said space by moving said piston, said conduit being adapted to be attached to a supply of drench and having an opening providing communication between the interior of said conduit and said space, and valve means restricting movement of drench through the gun so that the drench exits from said nozzle.

A preferred form of the present invention will now be described by way of example with reference to the accompanying drawing which depicts in part section side elevation a drench gun.

The drench gun 10 includes a nozzle 22 which is adapted to be engaged within the mouth of a beast to receive a dosage of drench, with the end 23 of the nozzle 22 being located in the vicinity of the throat of the beast. Attached to the nozzle 22 is a central conduit 16 through which the drench passes and to which is attached a cylinder 11 having an end wall 24 and adapted with piston 13 to define a variable volume working space 14 to receive the drench.

The conduit 16 includes an opening 19 through which drench enters and leaves the space 14. The piston 13 includes recesses 21 to receive sealing elements 30 to engage the interior surface 12 of the cylinder 11. The piston 13 also includes an "O" ring 17 which slidably engages the outer surface of the conduit 16. Extending from and attached to the piston 13 is a sleeve 15 which includes a handle 25 to be gripped by a user of the gun 10. The sleeve 15 and piston 13 are slidable longitudinally of the conduit 16 to thereby vary the volume of space 14, since the cylinder 11 and end wall 24 thereof are fixed relative to the conduit 16. The end wall 24 includes a spigot 20 which communicates with the opening 19 via a passage 29 in plug 26. The plug 26 also attaches an end of the conduit 16 to the wall 24. The cylinder 11 is also supported in position by wall 27 which slidably engages the outer surface of the sleeve 15.

The sleeve 15 and cylinder 11 are biased apart by means of a spring 28, while there is also provided a trigger (not illustrated) on the handle 25 which prevents relative movement between the cylinder 11 and sleeve 15 until the trigger is actuated.

In use the nozzle 22 is located in the mouth of the beast by an operator holding the handle 25 and pulling back thereon to hold the nozzle 22 in position. Upon the actuation of the trigger on the handle 25, allowing relative movement between the cylinder 11 and sleeve 15, the user need only apply further pressure to the handle 25 to cause relative movement between the sleeve 15, and thus the piston 13, and the conduit 16 to decrease the volume of the working space 14. Such movement would compress spring 28. Upon the volume of the working space 14 decreasing, the drench located therein is forced through the opening 19 to exit through the end 23 of the nozzle 22. Upon pressure being released from the handle 25, the piston 13 will then be biased by means of spring 28 to the position defining a maximum volume of space 14, thereby increasing the volume of the working space 14 to draw drench in through the opening 19.

The drench is forced to move in a direction from right to left through the drench gun 10 by means of a one way valve located in the entrance portion, i.e. spigot 20 or plug 26, and a further one way valve located in the coupling 18 joining the conduit 16 to the nozzle 22. The spigot 20 is adapted to be attached to a liquid reservoir by means of a flexible conduit.

It is a notable advantage of this embodiment that the gun 10 may be operated by only one hand, thus freeing the other hand of the operator, for example, to hold the beast receiving the drench.

It is a still further advantage of the above embodiment that the piston 13 and sleeve 15 are rotatable about the conduit 16 and thus twisting of the beast's head during use of the gun will not result in twisting of the handle 25.

What I claim is:

1. A drench gun to deliver a dosage of drench into the mouth of a beast, said gun including a generally "U" shaped nozzle having a first extremity to be engaged within the mouth of the beast, a conduit having a first end portion attached to the other extremity of said nozzle and a second end portion extending therefrom in the general direction of extension of said first extremity, a hollow cylinder mounted on and encompassing said first end portion said conduit so as to be co-axial and co-extensive therewith, said cylinder being closed at one end and open at the other end which is located nearer said nozzle than said closed end, a piston slidably mounted on the conduit and slidably engaged within the cylinder so as to define within the cylinder a variable volume working space, biasing means biasing the piston towards the open end of said cylinder a sleeve fixed to the piston and slidably mounted on said conduit and extending from within said cylinder, handle means rigidly attached to said sleeve and extending laterally therefrom enabling it to be gripped by a user of the gun to vary the volume of said space by moving said piston, means for connecting said first end portion of said conduit to a supply of drench, said conduit having an opening providing communication between the interior of said conduit and said space, and valve means restricting movement of drench through said conduit so that the drench exits from said nozzle.

2. The drench gun of claim 1 wherein the sleeve and piston are rotatable about the longitudinal axis of the conduit.

3. The drench gun of claim 1 or 2 wherein the sleeve and cylinder are biased apart by a spring.

4. The drench gun of claim 1 or 2 wherein the sleeve has extending from it a handle to be gripped by the user.

* * * * *